United States Patent [19]

Souza

[11] Patent Number: 5,244,882
[45] Date of Patent: Sep. 14, 1993

[54] PORCINE GROWTH HORMONE ANALOGS, AND COMPOSITIONS

[75] Inventor: Lawrence M. Souza, Thousand Oaks, Calif.

[73] Assignees: Amgen, Inc., Thousand Oaks, Calif.; SmithKline Beecham Corporation, Philadelphia, Pa.

[21] Appl. No.: 920,951

[22] Filed: Jul. 28, 1992

Related U.S. Application Data

[62] Division of Ser. No. 810,320, Dec. 19, 1991, abandoned, which is a division of Ser. No. 24,837, Mar. 12, 1987, Pat. No. 5,104,806.

[51] Int. Cl.$^5$ .................... A61K 37/02; A61K 37/36; C07K 7/10
[52] U.S. Cl. ..................................... 514/12; 530/399; 514/21; 514/806
[58] Field of Search ..................... 530/399; 514/12, 21, 514/806

[56] References Cited

U.S. PATENT DOCUMENTS

| | | | |
|---|---|---|---|
| 4,670,249 | 6/1987 | Ivy et al. | 424/424 |
| 4,699,897 | 10/1987 | Jones et al. | 514/4 |
| 4,765,980 | 8/1988 | DePrince et al. | 424/108 |
| 4,792,546 | 12/1988 | Baker | 514/12 |
| 4,861,868 | 8/1989 | Krivi | 530/399 |
| 5,037,806 | 8/1991 | Krivi | 514/12 |
| 5,134,120 | 7/1992 | Boyd et al. | 514/12 |

FOREIGN PATENT DOCUMENTS

| | | |
|---|---|---|
| 111389 | 6/1984 | European Pat. Off. |
| 193515 | 9/1986 | European Pat. Off. |

OTHER PUBLICATIONS

Seeburg, P. et al., *DNA*, 2(1):37–45, 1983.
Lewis, U. et al., *Biochem. Biophys. Res. Comm.*, 92(2):511–516, 1980.
R. D. Boyd, et al., J. Animal Sci. 66 (Supp 1), 1988 (Abst).

*Primary Examiner*—Robert J. Hill, Jr.
*Assistant Examiner*—Marianne Porta Allen
*Attorney, Agent, or Firm*—Herbert H. Jervis; Steven M. Odre; Edward T. Lentz

[57] ABSTRACT

An analog of porcine growth hormone, is disclosed which retains the diabetogenic, insulin-sparing and lipolytic properties of porcine growth hormone while being capable of improving growth in mammals.

4 Claims, 4 Drawing Sheets

PORCINE GROWTH HORMONE ANALOGS, AND COMPOSITIONS

This is a divisional of copending application(s) Ser. No. 07/810,320 filed on Dec. 12, 1991, now abandoned, which is a divisional of Ser. No. 07/024,837 filed on Mar. 12, 1987, now U.S. Pat. No. 5,104,806.

BACKGROUND

The present invention relates to a class of novel analogs of porcine growth hormone. In particular, the present invention pertains to recombinantly-produced analogs of porcine growth hormone wherein one or more residues corresponding to the residues at positions 32 through 38 in the amino acid sequence of naturally occurring porcine growth hormone are deleted. The present invention further relates to compositions containing such analogs and to the use of such analogs and compositions to increase the growth of mammals.

The pituitary gland of normal mammals produces and secretes into the bloodstream a substance called growth hormone ("GH"). The amino acid sequences of human ("hGH"), bovine ("bGH"), and porcine ("pGH") growth hormones are similar. See Dayhoff, *Atlas of Protein Sequence and Structure*, Volume 5, Supplement 6, National Biomedical Research Foundation, Washington, 120–121 (1976); and Seeburg et al., DNA, 2, 37–45 (1983). The amino acid and nucleotide sequences of salmon growth hormone ("sGH") is also known, Sekine et al., *Proc. Nat'l. Acad. Sci. (USA)*, 82, 4306–4310 (1985). Based upon an alignment of the sequences of bGH, hGH, evine growth hormone, pGH, and sGH which provides the highest degree of homology among these growth hormones, certain highly conserved regions may be identified. See e.g., Dayhoff, supra, and Sekine et al., supra.

In vivo, growth hormone promotes construction of protein from amino acids, an initial fall in plasma glucose upon administration, a gradual rise in plasma glucose after the initial fall, and a breakdown of fats into fatty acids. The effects associated with growth hormone are respectively referred to as growth promotion (i.e., weight gain), insulin-sparing, diabetogenic and lipolytic effects. An antilipolytic effect has also been reported, but this appears to be a facet of the insulin-like activity of the hormone. Goodman, *Metabolism*, 19, 849–855 (1970).

In addition, growth hormones are similar in structure to lactogenic hormones and are capable of inducing similar effects. For example, hGH differs from the human placental lactogen at about 15% of its residues. Wallis et al., in *Growth Hormone and Related Peptides*, Pecile et al., eds., Excerpta Medica, Amsterdam, 1–13 (1976). Human growth hormone differs from human prolactin at about 25% of its residues. Wallis et al., supra. Subcutaneous injection of bGH or recombinant bGH ("rbGH") increases milk yield in cows, goats and sheep. Eppaird et al., *J.Dairy Sci.* 68, 1109–1115 (1985); Bauman et al., *J. Dairy Sci.*, 68, 1352–1362 (1985); Hart, *Proc. Nutr. Soc.*, 42, 181–194 (1983); and see Hart et al., *Biochem. J.*, 218, 573–581 (1984).

The isolation of growth hormone from pituitaries involves lysing pituitary cells associated with production of the hormone. However, the lysing of cells releases proteolytic enzymes (proteases) which may cleave at least some of a naturally-occurring pituitary growth hormone ("nGH") into fragments. Furthermore, once secreted into the bloodstream, nGH is exposed to proteases which may cleave nGH into the same or into different fragments. A major area of investigation for growth hormone fragment research is directed at a determination of whether nGH or its fragments or both give rise to the actions associated with growth hormones which have been extracted or which are circulating in the bloodstream. In this regard, it may be noted analogs of hGH rendered resistant to digestion by the protease trypsin by chemically modifying lysine or arginine residues possess significant, albeit attenuated, growth-promoting, diabetogenic and insulin-like activities. Cameron et al., *Biochim. Biophys. Acta*, 254–260 (1985). Nevertheless, discrete portions ("domains") of the nGH molecule are believed to be responsible for one or another of the effects of nGH. To the extent that responsibility for the actions of nGH may be localized in this way, fragments and analogs may be produced in which the protein-synthetic, insulin-sparing, diabetogenic and lipolytic effects are selectively altered.

As used hereinafter, the positions of amino acid residues present in fragments or analogs of growth hormone are identified in a subscript wherein numbers indicate the presence of the residues found at the same positions in the corresponding nGH and wherein deletions are indicated by a comma. For example, naturally occurring porcine growth hormone is represented by $pGH_1$-190.

A 20,000-dalton variant ("20K") of hGH (22,000-dalton) which may be isolated from pituitaries and which corresponds to $hGH_1$-31,47-191 promotes growth in hypophysectomized rats, is not hyperglycemic or hyperinsulinemic in dogs, is neither insulin-sparing nor lipolytic in vivo or in vitro, and is less reactive in radioimmunoassays for hGH than is hGH itself. Lewis et al., *J. Biol. Chem.*, 253, 2679–2687 (1978); Frigeri et al., *Biochem. Biophys. Res. Commun.*, 91, 778–782 (1979); Lewis et al., *Biochem. Biophys. Res. Commun.*, 92, 511–516 (1980); and Lewis et al., *Endocr. Res. Commun.*, 8, 155–164 (1981). The 20K variant of hGH is a product of post-transcriptional modification. Lewis et al., *Biochem. Biophys. Res. Commun.*, supra. It may be the case that the 20K variant of hGH may be a more important growth promoter than would be predicted from its in vitro bioactivity due to its tendency to dimerize and thus escape renal degradation. Baumann et al., *Endocrinology*, 117, 1309–1313 (1985).

Fragments of hGH which include residues deleted from 20K hGH have also been disclosed. Although none of these fragments are reported to promote growth, some exhibit properties of potential relevance to the diabetogenic and lipolytic properties of growth hormone.

A synthetic fragment corresponding to residues 31–44 of hGH is lipolytic in vivo in starved animals and in vitro [Yudaev, et al., *Biokhimiya*, 41, 843–846 (1976)] but stimulates glucose uptake (i.e. was insulin-sparing) only after in vitro preincubation in the absence of GH, a non-physiological state. Yudaev, et al., *Biochem. Biophys. Res. Commun.*, 110, 866–872 (1983). Some peptides analogs of hGH are diabetogenic but an analog of $hGH_{52}$-77 is not. Lostroh, et al., *Diabetes*, 27, 597–598 (1978). A peptide consisting of $hGH_{20}$-41 is devoid of activity. Reagan, Diabetes, 27, 883–888 (1978). A peptide consisting of $hGH_1$-36 is devoid of effect on blood glucose or on growth. Chillemi, et al., in *Growth Hor-* mone and Related Peptides, Pecile, et al., eds., Excerpta Medica, Amsterdam, 50–63, (1976).

However, a peptide corresponding to hGH$_{32}$-46 causes a decrease in serum free fatty acids, and is insulin-sparing when coadministered with insulin in vitro [Frigeri et al., in *Proceedings*, 64th Annual Meeting of the Endocrine Society, San Francisco, 101 (Abstract 88) (1982)] and in vivo [Rudman, U.S. Pat. No. 4,558,033, and Stevenson et al., *Diabetes*, 33, 149A (Abstract No. 572) (1984)]. Fragments and analogs (involving substitution of heterologous amino acids or stereoisomers) of hGH$_{32}$-46 are also insulin-sparing when coadministered with insulin in vivo. Jones et al., copending and coassigned U.S. patent application Ser. No. 501,024 now U.S. Pat. No. 4,699,897.

SUMMARY OF THE INVENTION

The present invention relates to a class of porcine growth hormone analogs which retains the biological activity and properties of naturally occuring porcine growth hormone while increasing the growth rate, feed efficiency, increased lypolysis or milk yields.

In particular, the present invention relates to a recombinant porcine growth hormone analog comprising the amino acid sequence

Z-pGH$_{1-31}$-(X)$_n$-pGH$_{39-190}$ wherein
n is 0 or 1;
Z is hydrogen, MET, ALA or MET-ALA-; and
X is a peptide of an amino acid residue(s) comprising

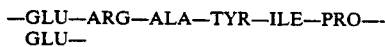

—GLU—ARG—ALA—TYR—ILE—PRO—GLU— wherein one or more of the amino acids are deleted; and allelic versions thereof.

The invention further relates to a synthetic gene encoding porcine growth hormone analogs having the above described sequence. The present invention also relates to processes of construction of various replicable cloning vehicles harboring the DNA sequences as well as expression vehicles harboring DNA sequences useful to direct the production of the porcine growth hormones analogs in transformed bacteria or transfected cell lines. In addition, the present invention provides for a gene encoding the analogs of porcine growth hormone having the above-described amino acid sequence. The present invention also encompasses the various replicable cloning vehicles, expression vehicles, and transformed bacterial or cell cultures, all harboring the altered genetic information necessary to effect the production of the porcine growth hormone analogs of the present invention.

The porcine growth hormone analogs of the present invention are produced in substantially pure form and therefore exist essentially free of other proteins of porcine origin. The porcine growth hormone analogs may be formulated with conventional suitable carriers and adjuvants, including other proteins, for example, serum albumin, to yield acceptable compositions so as to facilitate efficacious delivery to a host animal.

The present invention also provides a method for promoting growth in an animal which involves administering to an animal an effective dose of a porcine growth hormone analog of the present invention.

DETAILED DESCRIPTION

Figure 1:
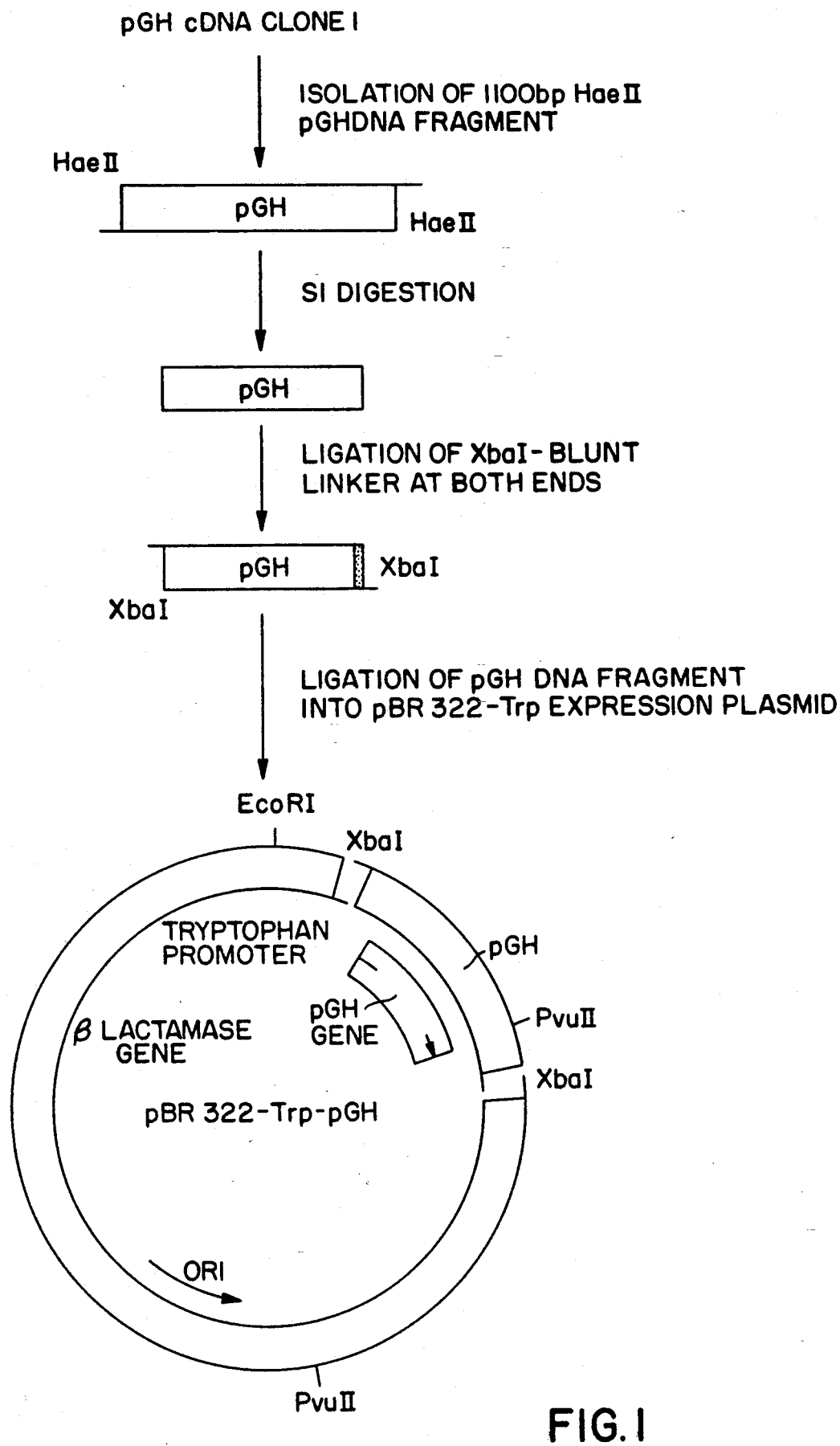
FIG. 1 is a schematic illustration of the pBR 322-Trp-pGH plasmid construction.

As previously discussed, the physiological activities of growth hormones may be attributed to the different domains of the intact polypeptide. Such activities may also be due to a particular folding or modification of the intact polypeptide, to the release of mediating factors, or to "contamination" by other pituitary peptides, e.g. α- and β-lipotropin which themselves can be responsible for lipolytic activity [Kuhn et al., *J. Clin. Endocrinol. Metab.*, 56, 1338–1340 (1983)]. Frigeri et al., *Hormone Res.*, 17, 197–201 (1983).

One way to separate the effects of contaminants from the effects of purified hormones is to examine the activities of a growth hormone which is produced in isolation from other pituitary components, e.g. recombinant pGH ("rpGH"). The gene for pGH has been sequenced and has been expressed in prokaryotic and eukaryotic cells in a variety of forms. Keshet et al., *Nucleic Acids Res.*, 9, 19–30 (1981); Woychik et al., *Nucleic Acids Res.*, 10, 7197–7210 (1982); Seeburg et al., *DNA*, 2, 37–45 (1983); Kopchick et al., *DNA*, 4, 23–31 (1985); and George et al., *DNA*, 4, 273–281 (1985).

The present invention provides purified and isolated polypeptide products having one or more of the biological properties (e.g., immunological properties and in vitro biological activity) and physical properties (e.g., molecular weight) of naturally-occurring pGH. These polypeptides are also characterized by being the product of chemical synthetic procedures or of prokaryotic or eukaryotic host expression (e.g., by bacterial, yeast, higher plant, insect and mammalian cells in culture) of exogenous DNA sequences obtained by genomic cloning by cDNA cloning or by gene synthesis. The products of typical yeast (e.g., *Saccharomyces cerevisiae*) or prokaryote (e.g., *Escherichia coli* (*E. coli*) host cells are free of association with any mammalian proteins. The products of microbial expression in vertebrate (e.g., non-human mammalian and avian) cells are free of association with any human proteins. Depending upon the host employed, polypeptides of the invention may be glycosylated with mammalian or other eukaryotic carbohydrates or may be non-glycosylated. Polypeptides of the invention may also include an initial methionine amino acid residue (at position −1).

As used herein, the term "peptide of an amino acid residues" refers to peptide comprising the amino acids GLU—ARG—ALA—TYR—ILE—PRO—GLU wherein one or more amino acids have been deleted. For the purposes of the present invention, the deletion of the amino acids in the peptide thus described may be sequential or random.

The term "manufactured" as applied to a DNA sequence or gene shall designate a product either totally chemically synthesized by assembly of nucleotide bases or derived synthesized. As such, the term is exclusive of products "synthesized" by cDNA methods of genomic cloning methodologies which involve starting materials which are initially of biological origin.

As used herein, the term "allelic versions" refers to modifications of one or more amino acids in the sequence of the porcine growth hormone analogs of the present invention without altering the biological activity of the analog. Such allelic versions are readily ascertained by one of ordinary skill in the art.

It should be noted that if Z is MET—ALA, preferably the MET residue is processed off to yield an analog wherein Z is ALA. A preferred porcine growth hormone analog of the present invention comprises a porcine growth hormone analog of formula (I) wherein n is 0 and Z is ALA. Another preferred porcine growth hormone analog comprises a porcine growth hormone analog of formula (I) wherein n is 1, Z is ALA and X is a residue having the sequence: —GLU—ARG—ALA—GLU—("ALA—pGH$_{1-34,38-190}$").

A further preferred porcine growth hormone analog of the present invention comprises an analog of formula (I) wherein n is 1, Z is ALA and X a residue having the sequence: GLU—ARG—ALA—TYR—ILE—GLU ("ALA—pGH$_{1-36,38-190}$"). An additionally preferred porcine growth hormone analog of the present invention comprises an analog of formula (I) wherein n is 1, Z is ALA and X is a residue having the sequence: —GLU—ALA—TYR—ILE—PRO—GLU—("ALA—pGH$_{1-32,34-190}$").

Table 1 represents the amino acid sequence of naturally occurring pGH.

TABLE 1

```
                                                                    -10                                          -1
pGH          ACC TCC GTG CTC CTG GCT TTC CTG CTG CCC CTG TGC CTG TGG ACT CAG GAG GTG GGA GCC
             thr ser val leu leu ala phe leu leu pro leu cys leu trp thr gln glu val gly ala
                                           10                                            20
pGH  TTC CCA GCC ATG CCC TTG TCC AGC CTA TTT GCC AAC GCC GTG CTC CGG GCC CAG CAC CTG GCT GCC
     phe pro ala met pro leu ser ser leu phe ala asn ala val leu arg ala gln his leu ala ala
                          30                                            40                                       50
pGH  GAC ACC TAC AAG GAG TTT GAG CGC GCC TAC ATC CCG GAG CAG AGG TAC TCC ATC AAC CAG CAG GCT GCC
     asp thr tyr lys glu phe glu arg ala tyr ile pro glu gln arg tyr ser ile asn gln gln ala ala
                          60                                            70
pGH  TTC TGC TTC TCG GAG ACC ATC CCG GCC CCC ACG GGC AAG GAC GAG GCC CAG CAG AGA TCG GAC GTG GAG CTG CTG
     phe cys phe ser glu thr ile pro ala pro thr gly lys asp glu ala gln gln arg ser asp val glu leu leu
                          80                                            90                                      100
pGH  CGC TTC TCG CTG CTC ATC CAG TCG TGG CTC GGG CCC GTG CAG TTC CTC AGC AGG GTC TTC ACC AAC AGC CTG
     arg phe ser leu leu ile gln ser trp leu gly pro val gln phe leu ser arg val phe thr asn ser leu
                          110                                           120
pGH  GTG TTT GGC ACC TCA GAC CGC GTC TAC GAC AAG CTG AAG GAC CTG GAG GAG GGC ATC CAG CTG ATG CGG GAG
     val phe gly thr ser asp arg val tyr asp lys leu lys asp leu glu glu gly ile gln leu met arg glu
                          130                                           140                                     150
pGH  CTG GAA GAT GGC AGC CCC CGG GCA GGA CAG ATC CTC AAG CAA ACC TAC GAC AAA TTT GAC ACA AAC TTG CGC AGT
     leu glu asp gly ser pro arg ala gly gln ile leu lys gln thr tyr asp lys phe asp thr asn leu arg ser
                          160                                           170
pGH  GAT GAC GCG CTT AAG AAC TAC GGG CTG CTC TCC TGC TTC AAG AAG GAC CTG CAC AAG CTG GAG ACA TAC CTG
     asp asp ala leu lys asn tyr gly leu leu ser cys phe lys lys asp leu his lys leu glu thr tyr leu
                          180                                           190
pGH  CGG CTC ATG AAG TGT CGC CGC TTC GTG GAG AGC AGC TGT GCC TTC
     arg val met lys cys arg arg phe val glu ser ser cys ala phe
```

The compositions and methods of the present invention utilize an effective amount or dose of the porcine growth hormone analogs of the present invention. As used herein, the term "effective amount or dose" of the porcine growth hormone analog refers to an amount of porcine growth hormone to be administered to an animal in order to produce an increase in growth or related properties, i.e., feed efficiency, leaner carcass composition, milk production, etc. Such effective amounts or doses are readily ascertained by one of ordinary skill in the art.

The following examples serve to further illustrate the embodiments of the present invention.

EXAMPLE 1

Sixty micrograms of polyadenylated RNA was isolated from one gram of porcine pituitaries. cDNA was generated from the polyA RNA via the procedures described by Okayama et al., *Mol. Cell. Biol.*, 2, 161 (1982) and transformed into an competent *E. coli* (strain HB101). Five thousand colonies were screened using a $^{32}$P-labeled nick-translated 493 bp PyuII cDNA bGH probe. Two hundred colonies hybridized from which five were carried through secondary screening, DNA isolation and restriction enzyme mapping. Two isolates contained approximately 900 bp of pGH cDNA sequence (1,4) and three contained approximately 700 bp (2,3,5).

Clone number 1 was carried through M13 DNA sequencing then transferred into a pBR322-Trp expression vector. To achieve this construction, plasmid DNA from clone 1 was cut at a HaeII site near the 5' end of the insert and at a HaeII outside the 3' end of the cDNA insert in the pBR322 region of clone 1, generating an 1100 bp fragment. This 1100 bp segment was SI nuclease treated and XbaI-Blunt linker was ligated to both ends. The XbaI bracketed DNA segment was then ligated into a pBR322-Trp expression plasmid that had been cut with XbaI (FIG. 1).

The XbaI-Blunt linker supplied a 5' XbaI site and 3' blunt end, as well as an ATG initiation codon.

<u>Xba</u> I
5' CTAGAGAATGGC 3'
3'     TCTTACCG 5'

Figure 2:
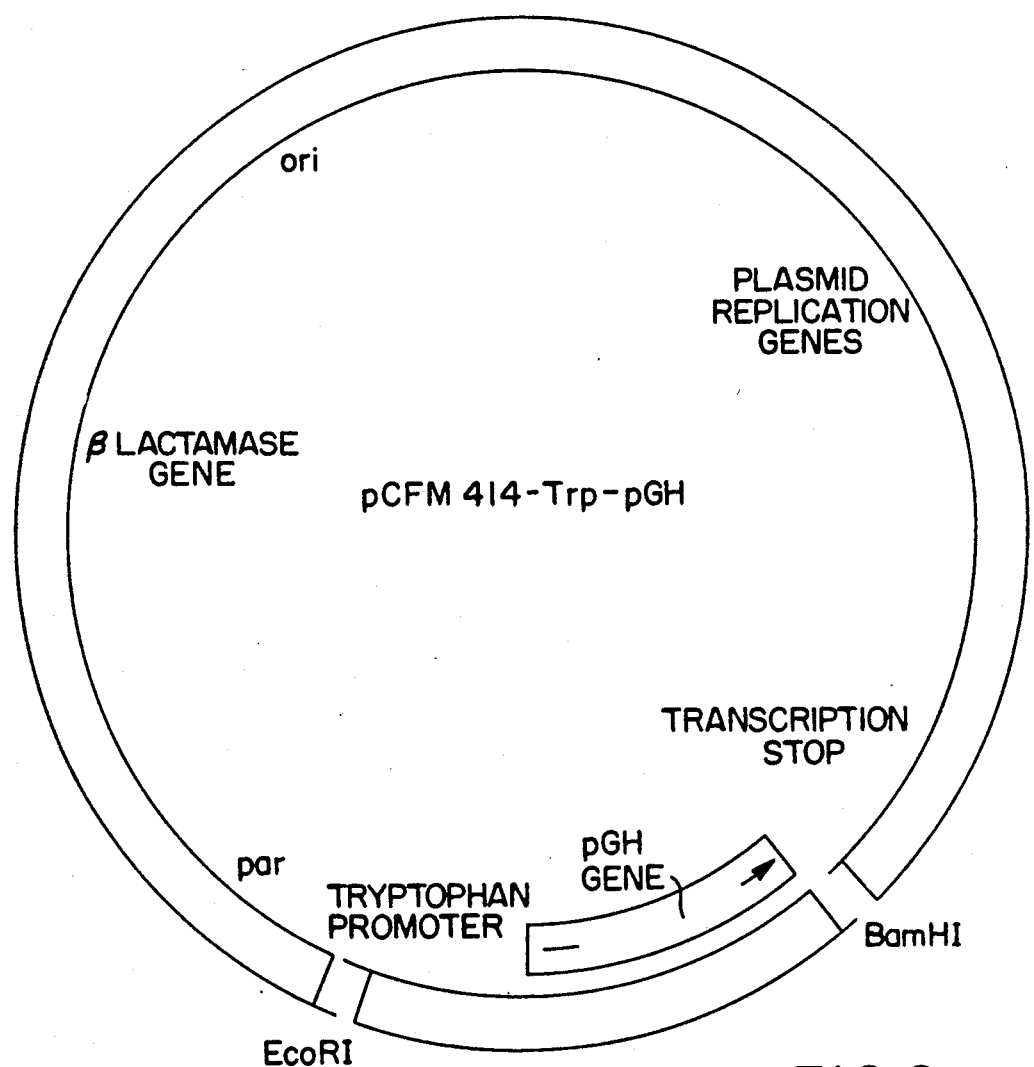
FIG. 2 is a schematic illustration of the pCFM 414-Trp-pGH plasmid construction.

The polyA tail at the 3' end was removed by carrying the above expression plasmid through a PvuII and EcoRI digestion to release the Trp/pGH 355 bp fragment. To this, a PvuII-BamHI linker was ligated at the PvuIII cut 3' end and this was then ligated into a pCFM expression plasmid that had been cut with the restriction enzymes EcoRI and BamHI (FIG. 2).

The PvuII-BAMHI linker contained one half of the PvuII site, a termination codons (TAA) and a BamHI site.

<u>PvuII</u>              <u>Bam</u> HI
5'CTGCGC ATTC TAA G          3'
3'GACGCG TAAG ATT CCTAG    5'

Based upon the sequencing data, two different double stranded (ds) oligonucleotide sequences were were chemically synthesized as described above (PGHwt, PGH-7). Each of these DNAs was assigned to have an XbaI restriction site at the 5' end and an ApaI restriction site at the 3' end. Just downstream of the ApaI site a HindIII restriction site was added to facilitate cloning into M13mp13 -bacteriophage.

Briefly stated, the protocol employed in the following examples to construct a manufactured gene was generally as set out in the disclosure of co-owned Alton, et al., PCT Publication No. WO83/04053, which is incorporated by reference herein. The genes were designed for initial assembly of component oligonucleotides into multiple duplexes which, in turn, were assembled into discrete sections. These sections were designed for ready amplification and upon removal from the amplification system, could be assembled sequentially or through a multiple fragment ligation in a suitable expression vector.

EXAMPLE 2

Figure 3:
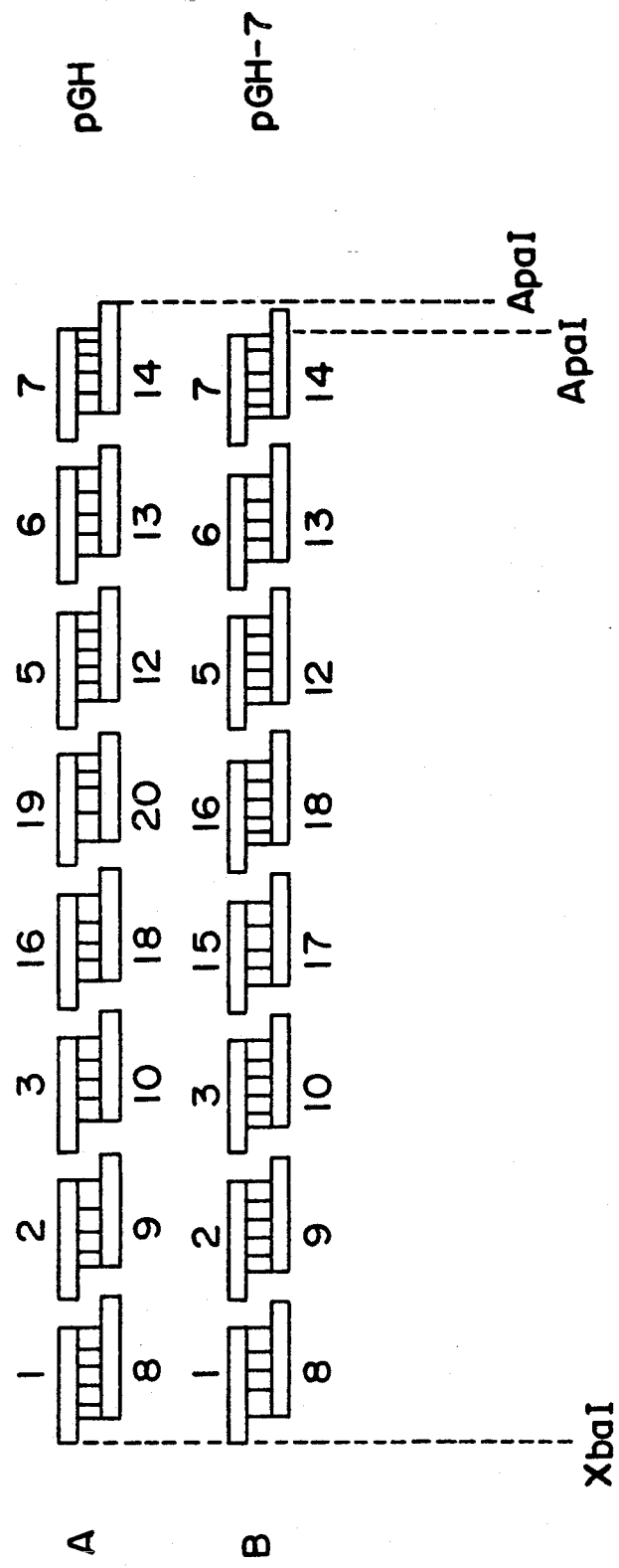
FIG. 3 is a diagrammatic description of the oligonucleotide assembly utilized to make the XbaI to ApaI pGH DNA fragments utilized in the construction of pGH and pGH-7.

Two gene fragments for porcine growth hormone were constructed in parallel. One gene fragment (Fragment 1-pGHwt) contained a 22K porcine growth hormone gene sequence as deduced by cDNA sequencing. A second gene fragment (Fragment 2-pGH-7) coded for the 22K porcine growth hormone sequence minus 7 amino acids in the "deletion peptide" (DP) region (hereinafter 21K porcine growth hormone). Oligomers 15, 16, 17 and 18 bridged the gap between the beginning and the end of the DP coding region in pGH-7 and code for the amino acids added in this gene version. Oligonucleotide segments common to both gene versions were 1, 2, 3, 5, 6, 7, 8, 9, 10, 12, 13, 14, 16 and 18 (FIG. 3).

The 20 oligonucleotides required for the construction of the two gene fragments were synthesized on an ABI DNA synthesizer and purified by gel electrophoresis using standard methods and are listed in Table 2. Each purified oligonucleotide (oligo) was dissolved in 1 ml of TE (10 mM Tris HCl, pH 7.2, 0.1 mM EDTA) and the absorbance at 260 nm was recorded. The absorbance was compared to the calculated extinction coefficient for the oligo and a concentration was computed. The concentration in picomoles per microliter was then used to measure the respective oligos for the gene constructions. For example, for oligo #1, a 39-mer containing 13 adenines, 8 cytosines, 9 guanines and 9 thymidines, the calculated extinction coefficient at 260 nm is 4447–00. The absorbance at 260 nm was measured as 0.379 and the resulting concentration in pm/microliter is 0.852. The oligos were measured using an Eppendorf pipetman into Eppendorf tubes. The amounts used were such that 100 picomoles of each oligo would be allotted to each gene fragment to be constructed. Thus, 200 pmole of oligos #1, 2, 3, 5, 6, 7, 8, 9, 10, 12, 13, 14, 16 and 18 were used since these are common to each of the two gene constructions. 100 pmole of oligos 15, 17, 19 and 20 were used since they are found in only one of the gene constructions. The measured oligos were speed-vac'd to dryness and then redried using 150 microliters of 80% ethanol, 20% water.

The oligos were selectively phosphorylated so that the oligomers which would ultimately be on the ends of the finished gene constructions could not selfligate. Thus oligos 1 and 14 were not phosphorylated. All the other oligos were phosphorylated. All kinations and ligations were done in ligation buffer, "LB", consisting of 50 mM HEPES, pH 7.6, 10 mM magnesium chloride and 10 mM dithiothreitol. (LB was stored as a ten-fold concentrated solution, 10X LB and diluted into water as needed.) Oligos 1 and 14 were each dissolved in 60 microliters of LB and set on ice until needed later.

A kinase mix was prepared which contained: 92 microliters 10X LB, 20 microliters polynucleotide kinase (Boehringer-Mannheim, 10 unit/microliter), 1 microliter 10 mM ATP, in TE, ¼ microliter 32-phosphorus gamma, phosphate ATP containing 80,000,000 counts/minute of radioactivity, 810 microliters water.

The total volume of the kinase mix was 920 microliters. The mix was added to the dried oligos, 20 microliters for each 100 pmole to be phosphorylated. Oligos 2, 3, 5, 6, 7, 8, 9, 10, 12, 13, 16 and 18 (200 pmole each) were each dissolved in 40 microliters of kinase mix. Oligos 15, 17, 19 and 20 (100 pmole each) were dissolved in 20 microliters of kinase mix. All the tubes containing the dissolved oligos in kinase mix were then incubated at 37° C. for 45 minutes. A ¼ microliter aliquot was removed from each tube and spotted separately on a DE-81 paper strip. The DE-81 strips were then eluted in a chromatography chamber with 0.35M ammonium formate buffer until the solvent front reached the bottom of the descending strip. The strips were then removed from the chamber, dried in a 100° C. drying oven and cut into pieces for analysis in a liquid scintillation counter (Beckman LS 6800). The strips were cut such there was one piece containing only the origin and a second piece which contained the rest of the DE-81 strip. The fragments from the DE-81 strip were then placed in plastic counting vials and counted dry in the LS-6800. The counter showed radioactivity incorporated at the origin of each strip and so the phosphorylation reactions were chased with a large excess of cold ATP. One microliter of 10 mM ATP was added to each phosphorylation reaction and the tubes were incubated at 37° for an additional 45 minutes following the DE-81 analysis. All oligo containing tubes (including 1 and 14 which were not phosphorylated) were then boiled for 5 minutes and quickly cooled. This process destroyed the kinase enzyme.

1+8

2+9

3+10

5+12

6+13

7+14

15+17

16+18

19+20

Each duplex took the name of the first oligo in the pair. Tubes 1, 2, 3, 5, 6, 7, 15, 16 and 19 were mixed, boiled for 5 min. and then slow cooled to room temperature.

These annealed duplexes were then combined to form tetramers:

3+2

5+6

These tetramers took the name of the first tube in the pair, 3 and 5, respectively. To each of tubes containing tetramers 3 and 5 were added 5 microliters of 10 mM ATP (to give approximately 200 micromolar ATP concentration) The tetramers were annealed at 37° for 10 minutes. Five microliters of ligase (Boehringer-Mannheim, 1 unit/microliter) were added to each tube. The ligations were incubated for 5 minutes at 37° and then for 1 hour on ice.

One-half of duplex 16 was combined with duplex 15 and the remaining ½ with duplex 19. To each of these tetramers were added 2 microliters of 10 mM ATP. The tetramers were annealed at 37° for 10 minutes, then 2 microliters of ligase were added to each tube. The mixtures were incubated 5 minutes at 37° and for one hour on ice.

More duplexes were added to yield longer duplexes: duplex 7 added to tetramer 5, yielding hexamer #5; duplex 1 added to tetramer 3, yielding hexamer #3; 2.5 microliters 10 mM ATP and 2.5 microliters ligase were added to these hexamers. The two tubes were then mixed, incubated for 10 minutes at 37° and for one hour on ice.

One-third of hexamer #5 was added to each of tubes 15 and 19 containing the central oligos of pGH-7 and pGH, respectively. The tubes 15 and 19 were incubated 10 minutes at 37° and 2 hours on ice. Then hexamer #3 was added, ½ to each of tubes 15 and 19. All oligos required for construction of 10 mM ATP and 5 microliters of ligase were added to each of the tubes. The tubes containing the ligation mix were incubated for minutes at 37° and at 4° for 5 days.

Five microliters from each of the three ligations were checked on a 0.75 mm thick analytical polyacrylamide gel, 5%, 7M urea. 32-P labeled HpaII cut pBR322 was run in an adjacent lane as a standard. The aliquots from each ligation as well as the HpaII standard were diluted into 20 microliters of 80% formamide 20% water containing 0.1% xylene cyanol and bromphenol blue dyes (80% formamide plus dyes). The samples were boiled for 5 minutes then quick chilled on ice and loaded onto the gel. The gel was run at 400 volts for 45 minutes (until the bromphenol blue reached the bottom of the gel slab) then removed from the glass plates, wrapped in Saran Wrap and placed in a film cassette with a sheet of Dupont Cronex X-ray film. Exposure at −70° C. and developing of the film caused the ligated DNA to be visualized on the autoradiogram. In lane 15 was a band corresponding to a 272 base pair duplex. In lane 19 was a band corresponding to a 293 base pair duplex. This indicated that each ligation had proceeded to give some of the desired DNA construct for pGH-7 and pGH, respectively.

Based on the analytical gel results, the three ligation mixtures were prepared for large scale gel purification. Each ligation was ethanol precipitated using 40 microliters of 3M sodium acetate and 1 ml of 100% ethanol and chilling at −70° C. overnight. After a 10 minute centrifugation at 10000 times g, the DNA pellet was isolated by removing the supernatant and rinsing with 100 microliters of ice cold 80% ethanol. The rinsed pellets were speed-vac'd to dryness. Each pellet was then dissolved in 80 microliters of 80% formamide with dyes. They were boiled for 5 minutes and quick chilled on ice. ½ of each ligation mixture was then loaded onto a 3 mm thick 5% polyacrylamide gel containing 7M urea. The gel was run at 250 to 300 volts for 2 hours. The gel was then placed into a film cassette and autoradiographed at room temperature to visualize the bands. The developed film was then placed next to the gel in the cassette, the position of the band in each lane corresponding to the fully ligated gene fragment was marked and the desired bands were cut out of the gel using a razor blade. Each gel slice was then pulverized by extruding it through a 3 ml syringe (without needle) into an Eppendorf tube. Each pulverized gel slice was covered with 0.7 ml of gel elution buffer (0.5M ammonium acetate, 0.01M magnesium acetate, 0.001M EDTA and 0.1% ammonium acetate, 0.01M magnesium acetate, 0.001M EDTA and 0.1% sodium dodecyl sulfate) and incubated overnight at 37° C.

The gel-solution mixture was filtered through a glass fiber filter pad in a syringe barrel and washed 3 times with n-butanol. The DNA was precipitated by addition of 2½ volumes of ethanol and storage at −70° for 1 hour. Centrifugation for 10 minutes at 1000 times g gave pellets which were isolated by decanting the supernatant. The pellets were speedvac'd for 5 minutes to dry them. They were redissolved in 200 microliters of TE, centrifuged to concentrate the polyacrylamide residue and then reprecipitated with 20 microliters 3M sodium acetate and 550 microliters of 100% ethanol. The dried DNA pellets were counted on the liquid scintillation counter and found to contain about 1 picomole of each gene fragment.

Each DNA pellet was redissolved in 20 microliters of solution containing 2 microliters of 10X LB and 1 microliter of radiolabeled ATP (30,000,000 cpm per microliter). One-fourth microliter aliquots were removed from each tube and spotted onto DE-81 strips. One microliter of polynucleotide kinase was added to each tube and the tubes were incubated at 37° for 30 minutes. One-fourth microliter aliquots were removed from the phosphorylation reactions and spotted onto another set of DE-81 strips. All six strips were then eluted with 0.35M ammonium formate and their origins compared for retained radioactivity. Comparison of the before and after DE-81 strips for each duplex showed that phosphorylation had occurred so each reaction was chased with 1 microliter 10 mM ATP to complete the reaction. After 45 minutes incubation at 37°, the tubes were boiled for 5 minutes and allowed to slow cool to room temperature. The annealed phosphorylated duplexes in ligation buffer were ready for ligation into the appropriately cloning vectors.

After cloning each of the synthetic pGH constructions into M13mp19, single stranded (ss) and ds DNAs were isolated. The ss DNAs were sequenced. The ds DNAs were used as sources of an XbaI to ApaI ds DNA fragments containing the 5' portion of the three different pGH constructions.

Figure 4:
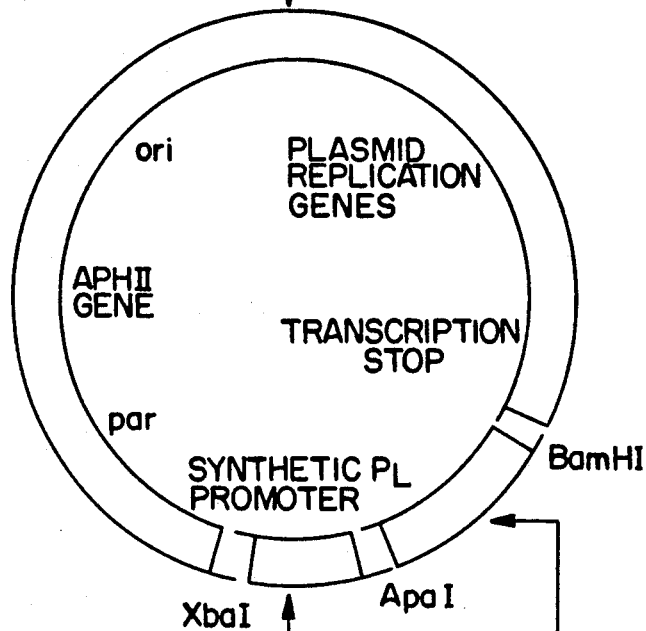
FIG. 4 is a diagrammatic illustration of the components utilized in the construction of pCFM 846-pGH plasmid.
Figure 4:
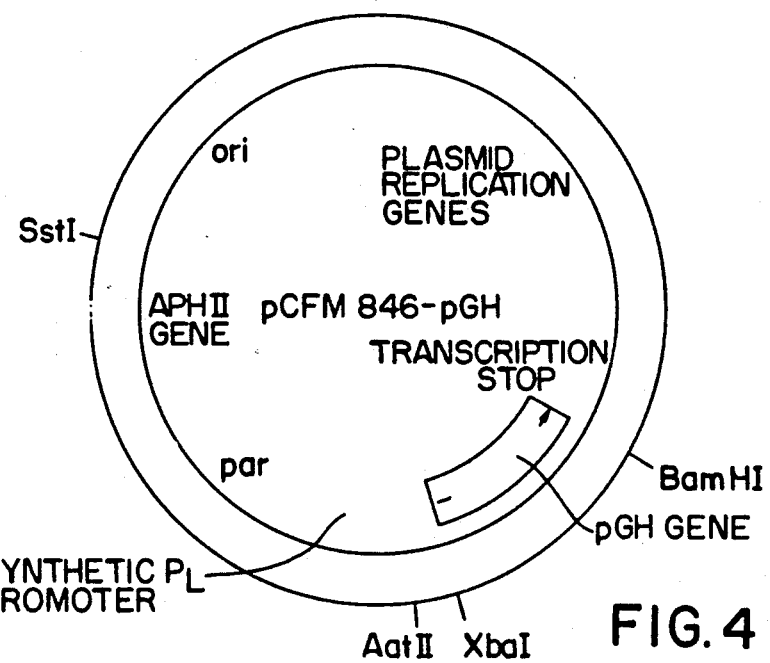

To construct the pGH expression vectors three way DNA ligations were required (FIG. 4). Component 1 was the XbaI to ApaI ds DNA fragment isolated from one of the three pGHmp19 DNAs. Component 2 was isolated from a pCFM414pGH vector as an ApaI to BamHI ds DNA fragment containing the 3' of the pGHwt gene. Component 3 was a pCFM846 plasmid cut with XbaI and BamHI. The pCFM846 plasmid is a derivative of pCFM836 (described below) prepared by inserting the following DNA sequence between the unique ClaI and KpnI site of pCFM836:

```
5' CGATTTGATTCTAGAATTCGTTAACGGTAC 3'
3'     TAAACTAAGATCTTAAGCAATTGC     5'
```

The plasmid pCFM836 is prepared as a derivative of PCFM536 (ATCC#39934) constructed to incorporate a Kanamycin resistance marker, a synthetic Pl promoter, a new cloning cluster of restriction sites, and a series of translational stop sequences designed to stop translation in all three reading frames. The B-lactamase gene is first deleted by digestion of pCFM536 with SstI and XbaI. This serves to delete not only the marker gene but also the entire "par" or stability sequence, the Pl promoter, and part of the cluster of restriction sites. The Kanamycin gene sequence may be obtained as a SmaI to HindIII fragment from the Tn5 plasmid of Beck et al., *Cold Spring Harbor Symp. Quant. Biol*, 45, pp. 107-113 (1981). To prepare the fragment for insertion into the new vector, a SstI linker is added to the SmaI site and an NdeI linker added to the HindIII site. The naturally occurring NcoI restriction site in the Kanamycin resistance gene was destroyed by site specific mutagenesis at the codon for a threonine residue 76 amino acids upstream of the carboxy terminal leucine specified by the Kanamycin resistance gene and specifically by altering the ACC codon to an ACT codon. The "par" locus sequence may be obtained as a HincII to AvaI digestion fragment of pSC101 (ATCC#37032). To prepare the "par" fragment for insertion into the new vector, the HincII is first treated with a SalI linker and then an AatII linker. The AvaI site is treated with a BamHI linker and then an NdeI linker. A DNA sequence containing a synthetic $P_L$ promoter obtained by chemical synthesis of a ds DNA oligonucleotide with sticky ends for insertion between an AatII restriction site and an XbaI restriction site was added as follows:

TABLE 2

| | | |
|---|---|---|
| 1 | 5' - | CTAGAAGGAGGAATAACATATGGCTTTTCCAGCAATGCC - 3' |
| 2 | 5' - | TCTCTCGAGCCTGTTCGCTAACGCTGTACTGCGTGCTCAG - 3' |
| 3 | 5' - | CACCTGCATCAACTGGCTGCAGACACTTACAAAGA - 3' |
| 5 | 5' - | TCCCGGCGCCAACTGGTAAAGACGAAGCTCAACA - 3' |
| 6 | 5' - | GAGATCTGATGTTGAACTGCTGCGTTTCTCT - 3' |
| 7 | 5' - | CTGCTGCTGATTCAATCTTGGCTGGGGCCCTTCA - 3' |
| 8 | 5' - | GAGAGGCATTGCTGGAAAAGCCATATGTTATTCCTCCTT - 3' |
| 9 | 5' - | AGGTGCTGAGCACGCAGTACAGCGTTAGCGAACAGGCTCGA - 3' |
| 10 | 5' - | GAATTCTTTGTAAGTGTCTGCAGCCAGTTGATGC - 3' |
| 12 | 5' - | TCTCTGTTGAGCTTCGTCTTTACCAGTTGGCGCC - 3' |
| 13 | 5' - | GCAGAGAGAAACGCAGCAGTTCAACATCAGA - 3' |
| 14 | 5' - | AGCTTGAAGGGCCCCAGCCAAGATTGAATCAGCA - 3' |
| 15 | 5' - | ATTCGGTCAGCGTTACTCTATC - 3' |
| 16 | 5' | CAGAACGCTCAGGCTGCATTTTGCTTCTCTGAAACCA - 3' |
| 17 | 5' | TTCTGGATAGAGTAACGCTGACC - 3' |
| 18 | 5' | GGGATGGTTTCAGAGAAGCAAAATGCAGCCTGAGCG - 3' |
| 19 | 5' | ATTCGAACGTGCTTACATCCCGGAAGGTCAGCGTTACTCTATC - 3' |
| 20 | 5' | TTCTGGATAGAGTAACGCTGACCTTCCGGGATGTAAGCACGTTC - 3' |

```
5'     CAGATCCATAAATTATCTCTGGCGGTGTTGACATAAATAC-
3'     TGCAGTCTAGGTATTTAATAGAGACCGCCACAACTGTATTTATG-

-CACTGGCGGTGATAATGAGCACATCGATT     3'
-GTGACCGCCACTATTACTCGTGTAGCTAAGATC 5'
```

To add the translation stops in all three frames the plasmid was cut with BamHI and the following ds oligonucleotide inserted:

```
5'   GATCCGCGGATAAATAAGTAAC   3'
3'       GCGCCTATTTATTCATTGCTAG 5'
```

After ligation each of the constructions was transformed into E. coli (strain FM6). FM6 is a derivative of AM7 (#CG608159) that has been rendered phage resistant to several unknown bacteriophages and contains the gene encoding tetracycline resistance and the lambda bacteriophage repressor genes, CI857 and cro, integrated into the chromosome.

After transformation, representative clones for each type of pGH were picked. Covalently closed circular (ccc) plasmid DNA was isolated and sequence using the alkaline denatured ccc technique. The sequence of the synthetic portion of 21K pGH is given in Table 3.

The fourth clone (—Glu, Arg . . . Glu—) requires two sequential site directed mutageneses. The first primer (A) will remove the Glu, Arg. After this site directed mutagenesis, the single stranded DNA is purified and a second round of site directed mutagenesis is conducted with a second primer (B) which will remove the second Glu.

Analog 4 Primers:
A TACAAAGAATTCGCTTACATCCCG
B CTTACATCCCGGGTCAGCGTTA

EXAMPLE 4

A fermentation run was performed for each of 22K and 21K. Cell densities were reached up to an optical density of 65. The amount of porcine growth hormone or analog thereof formed varied from 50–75 mg/OD L (3–3.9 gm/L).

The runs were made using E. coli FM6/pCFM 856 pGH #3 (with 22K pGH) and #8 (with 21K pGH).

TABLE 3

```
        6          16         26         36         46
    CTAGAA GGAGGAATAA CATATGGCTT TTCCAGCAAT GCTTCTCTCG
           TT CCTCCTTATT GTATACCGAA AAGGTCGTTA CGGAGAGAGC 56         66         76         86         96        106
AGCCTGTTCG CTAACGCTGT ACTGCGTGCT CAGCACCTGC ATCAACTGGC TGCAGACACT
TCGGACAAGC GATTGCGACA TGACGCACGA GTCGTGGACG TAGTTGACCG ACGTCTGTGA 116        126        136        146        156        166
TACAAAGAAT TCGGTCAGCG TTACTCTATC CAGAACGCTC AGGCTGCATT TGCTTCTCT
ATGTTTCTTA AGCCAGTCGC AATGAGATAG GTCTTGCGAG TCCGACGTAA AACGAAGAGA 176        186        196        206        216        226
GAAACCATCC CGGCGCCAAC TGGTAAAGAC GAAGCTCAAC AGAGATCTGA TGTTGAACTG
CTTTGGTAGG GCCGCGGTTG ACCATTTCTG CTTCGAGTTG TCTCTAGACT ACAACTTGAC 236        246        256        266        276
CTGCGTTTCT CTCTGCTGCT GATTCAATCT TGGCTGGGGC CCTTCA
GACGCAAAGA GAGACGACGA CTAAGTTAGA ACCGACCCCG GGAAGTTCGA
```

EXAMPLE 3

In addition, four additional pGH analogs may be constructed by site directed mutagenesis. First, the small XbaI to BamHI fragment from p846pGH22K is cloned into M13mp10 and single stranded phage DNA is isolated. Primers for each of the analogs are synthesized and kinased and annealed to the single stranded DNA. The four dNTP's, ATP, T4 DNA ligase and the klenow enzyme are added to synthesize the second strand of the DNA containing the desired changes. The DNA is transfected into the host strain, JM103 and plaques are plated out. The correct clones are determined by hybridization to 32P-labeled primers of the analog sequence. Sequences are confirmed by dideoxy sequencing nd the XbaI to BamHI fragment from M13mp10 is cloned back into p846. The primers for the clones are listed below:

Analog 1: (Tyr, Ile, Pro) TCGAACGTGCT-GAAGGTCAGCG
Analog 2: (Pro) GTGCTTACATCGAAGGT-CAGCG
Analog 3: (Arg) CAAAGAATTCGAAGCT-TACATCCC Each of the above have a walkaway plasmid and a kanamycin drug marker for plasmid stability.

TABLE 1

| Ingredient | (Medium composition) | |
|---|---|---|
| | Batch (8L) | Feed (3L) |
| yeast extract | 40 gm | 400 gm |
| $(NH_4)_2SO_4$ | 30 gm | 15 gm |
| $K_2HPO_4$ | 56 gm | — |
| $KH_2PO_4$ | 64 gm | — |
| Dow P-2000 | 2 ml | — |
| Glucose | 40 gm | 1300 gm |
| $(MgSO_4-7H_2O)$ (1M) | 32 ml | 103 ml |
| Trace Metal Solution | 16 ml | 28 ml |
| Vitamin Solution | 16 ml | 28 ml |
| Kanamycin | 20 µg/ml | |

The fermentation runs were made in a batch-fed mode and under carbon limitation. A temperature of 30° C. and a pH of 7.0 were maintained. Dissolved oxygen was maintained at 50% air saturation. Samples were taken at regular intervals and growth and acetate levels were measured. pGH concentration was measured using Coomassie stained SDS-PAGE. Because of the lack of availability of pure pGH, pure bGH and IFN- α-Con were used as a standard. The gel was scanned using a Shimodzu integrator/scanner and the average of the two standards was used to calculate the concentration of pGH and percentage of total protein.

Cells were induced by raising the termperature to 42° C. at an OD of ~25 and were observed under a microscope for inclusion bodies. It contained 1-2 inclusion bodies after about 3-4 hr of induction. There was no pGH found in pre-induction samples from two analog runs. The results are shown in Tables 4 and 5 for wild type (22K) and analog (21K).

TABLE 4

Gel results for wild type pGH (22K)

| | Time of Fermentation (hr) | OD | Percentage of Total Protein | mg pGH/OD L |
|---|---|---|---|---|
| Start | 18.5 | 25.4 | Pre-induction 2 | 6–10 |
| Induction | 21.0 | 43.0 | 10–15 | 30 |
| | 23.0 | 47.0 | 20–25 | 35–40 |
| | 25.5 | 48.5 | 30 | 65 |
| | 27.5 | 52.7 | 30–35 | 70–75 |

TABLE 5

Gel results for Analog pGH (21K)

| | Time of Fermentation (hr) | OD | Percentage of Total Protein | mg pGH/OD L |
|---|---|---|---|---|
| Start | 18.5 | 24.8 | Pre-induction 0 | 0–negl. |
| Induction | 21.0 | 48.0 | 20 | 45 |
| | 23.0 | 63.0 | 25–30 | 65 |
| | 25.5 | 57.2 | 30–35 | 65–70 |
| | 27.5 | 58.3 | 30–35 | 60–65 |

As illustrated in these tables, a maximum amount of pGH (70–75 mg/OD L) was produced with the 22K pGH. With the 21K pGH analog it seems that the amount of analog produced peaked with OD and later with a decrease in OD it started going down, possibly due to proteolytic degradation. It shows that 5–6 hours after induction is probably the optimum time to stop fermentation.

EXAMPLE 5

The biological activity of recombinantly-produced analogs evaluated in hypophysectomized rats during a 10-day weight gain bioassay, using pituitary-derived porcine growth hormone as a standard.

The 21K pGH analog of the present invention and pituitary-derived pGH ("pd-pGH") preparations were injected at three doses each, twice daily in 0.1 ml volumes, by subcutaneous route to hypophysectomized female rats on days 0–9 following a 12-day acclimation period. The pd-pGH preparation was reconstituted from lyophilized form in pH 9.5 bicarbonate buffer (30 mM) to produce a stock solution having a concentration of 1 mg/ml. The stock solution was diluted, as were all recombinant samples, in "World Health Organization" ("WHO" buffer (0.2% lactose, 0.2% mannitol, 30 mM $NaHCO_3$, pH 8.6) to 300, 100, and 30 μg/ml. The samples were stored at 4° C. for the duration of the experiment. Protein determinations were conducted on aliquots of the test materials.

Chemical Analysis

The pd-pGH was found to be only 85% pGH monomer by protein chemical analysis, and therefore was administered at 1.18x the dose on the basis of lyophilized material weight out. All injection solutions were analyzed for protein content by Bradford assay, using BSA in WHO buffer as a standard. The preparations varied in matching the expected protein concentrations (Table 6). In the absence of accurate methods to determine protein concentrations of the pGH injectates by extinction coefficients, all actual doses were taken to be those indicated by the Bradford results.

Weight Gain

The rate of weight gain was accelerated in a dose-related manner by all preparations. Therefore, biological response was evaluated by the actual weight change from Day 0 to Day 10. The 21K pGH analog of the present invention induced greater weight gain than recombinant 22K pGH and pd-pGH at the lower two doses. The highest 21K pGH analog dose tested did not stimulate weight gain further, possibly because maximal rate had been achieved by lower doses. Table 7 lists the actual body weight changes. Table 8 displays relative potencies of each preparation as determined by linear regression analysis of log(dose) vs. change in body weight, using regression coefficients for the pituitary standards.

TABLE 6

| | Protein Concentrations of α Somatotropin Injectates (μg/ml) | |
|---|---|---|
| Sample | Expected [ ] | Actual [ ] (Bradford) |
| α pd-pGH* | 353 | 360 |
| | 118 | 118 |
| | 35 | 35 |
| pGH (21K analog) | 300 | 342 |
| | 100 | 127 |
| | 30 | 35 |
| pGH (21K analog) | 300 | 396 |
| | 100 | 138 |
| | 30 | 36 |
| pit-bGH "std." | 300 | 329 |
| | 100 | 109 |
| | 30 | 31 |
| pGH (21K analog) | 300 | 314 |
| | 100 | 104 |
| | 30 | 29 |
| pGH (21K analog) | 300 | 268 |
| | 100 | 90 |
| | 30 | 24 |

*Estimated only 85% pGH monomer by weight

TABLE 7

Based on Bradford [Protein]
Pituitary Vs. Recombinant Porcine Growth Hormone
Hypophysectomized Rat Weight Gain Assay TRL 031-017
(change in body weight, grams mean +/− SEM)

| DOSE α (μg/rat/day) | BUFFER | pit-bGH std. (pituitary) | 22K pGH | 21K pGH |
|---|---|---|---|---|
| 0 | 1.5 +/− 0.6 | | | |
| 7.0 | | 14.3 +/− 0.7 | 13.9 +/− 1.1 | |
| 7.2 | | | | 20.7 +/− 1.1 |
| 23.6 | | 19.4 +/− 0.8 | | |
| 25.4 | | | 23.6 +/− 1.2 | |
| 27.6 | | | | 28.4 +/− 1.2 |

TABLE 7-continued

Based on Bradford [Protein]
Pituitary Vs. Recombinant Porcine Growth Hormone
Hypophysectomized Rat Weight Gain Assay TRL 031-017
(change in body weight, grams mean +/− SEM)

| DOSE α (μg/rat/day) | BUFFER | pit-bGH std. (pituitary) | 22K pGH | 21K pGH |
|---|---|---|---|---|
| 68.4 | | | 30.2 +/− 2.2 | |
| 72.0 | | 30.2 +/− 1.6 | | |
| 79.2 | | | | 29.6 +/− 3.9 |

TABLE 8

Relative Potency Equivalence of
Growth Hormone Preparations
(Mean ± standard error of the mean)

| Reference Preparation | Sample | Relative Equivalence to Reference Preparation |
|---|---|---|
| pit-bGH "std" | pit-bGH "std" | 1.01 ± 0.05 |
| pit-bGH "std" | 22K pGH | 1.06 ± 0.01 |
| pit-bGH "std" | 21K pGH | 1.40 ± 0.15 |

While the present invention has been described in terms of a preferred embodiment, it is expected that modifications and improvements will occur to those skilled in the art upon consideration of this disclosure. Accordingly, it is intended that the appended claims cover all such equivalents which come within the scope of the invention as claimed.

What is claimed is:

1. A procine growth hormone analog comprising the amino acid sequence represented by the formula $$Z\text{-pGH}_{1\text{-}31}\text{-pGH}_{39\text{-}190}$$

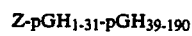

wherein Z is hydrogen, MET, ALA, or MET-ALA and which is essentially free of other proteins of porcine origin.

2. A procine growth hormone analog according to claim 1 wherein Z is ALA or MET-ALA.

3. A procine growth hormone analog according to claim 2 wherein in Z is ALA.

4. A composition comprising a porcine growth hormone analog of claim 1 in combination with a suitable carrier.

* * * * *

UNITED STATES PATENT AND TRADEMARK OFFICE
CERTIFICATE OF CORRECTION

PATENT NO. : 5,244,882

DATED : September 14, 1993

INVENTOR(S) : Lawrence M. Souza

It is certified that error appears in the above-identified patent and that said Letters Patent is hereby corrected as shown below:

At column 20, lines 14, 22, and 24, in claims 1, 2 and 3 respectively, "procine" should read --porcine--.

Signed and Sealed this

Fifteenth Day of March, 1994

Attest:

BRUCE LEHMAN

*Attesting Officer*  *Commissioner of Patents and Trademarks*